United States Patent [19]

Mechling

[11] Patent Number: 4,944,309

[45] Date of Patent: Jul. 31, 1990

[54] MEASURED VARIABLE RESISTANCE TILTBOARD

[76] Inventor: Richard W. Mechling, 830 Vedado Way NE., Atlanta, Ga. 30308

[21] Appl. No.: 280,360

[22] Filed: Dec. 6, 1988

[51] Int. Cl.$^5$ .............................................. A61B 5/10
[52] U.S. Cl. ...................................... 128/782; 272/146
[58] Field of Search ............... 128/25 R, 774, 782; 272/97, 146

[56] References Cited

U.S. PATENT DOCUMENTS

| | | | |
|---|---|---|---|
| 3,416,792 | 12/1968 | Morgan et al. | 272/146 |
| 3,702,188 | 11/1972 | Phillips et al. | 272/146 |
| 4,306,714 | 12/1981 | Loomis et al. | 272/126 |
| 4,548,289 | 10/1985 | Mechling | 128/774 |

*Primary Examiner*—Max Hindenburg
*Assistant Examiner*—Randy Shay

[57] ABSTRACT

An apparatus for the objective analysis of human balance reactions involving a pivotable platform with selectively variable resistance to platform rotation which provides for instantaneous measurement of the resistance applied against platform movement at any time during a balance test. Two devices to accomplish the measurement of resistance include use of an exercise dynamometer and use of strain gauges.

5 Claims, 2 Drawing Sheets

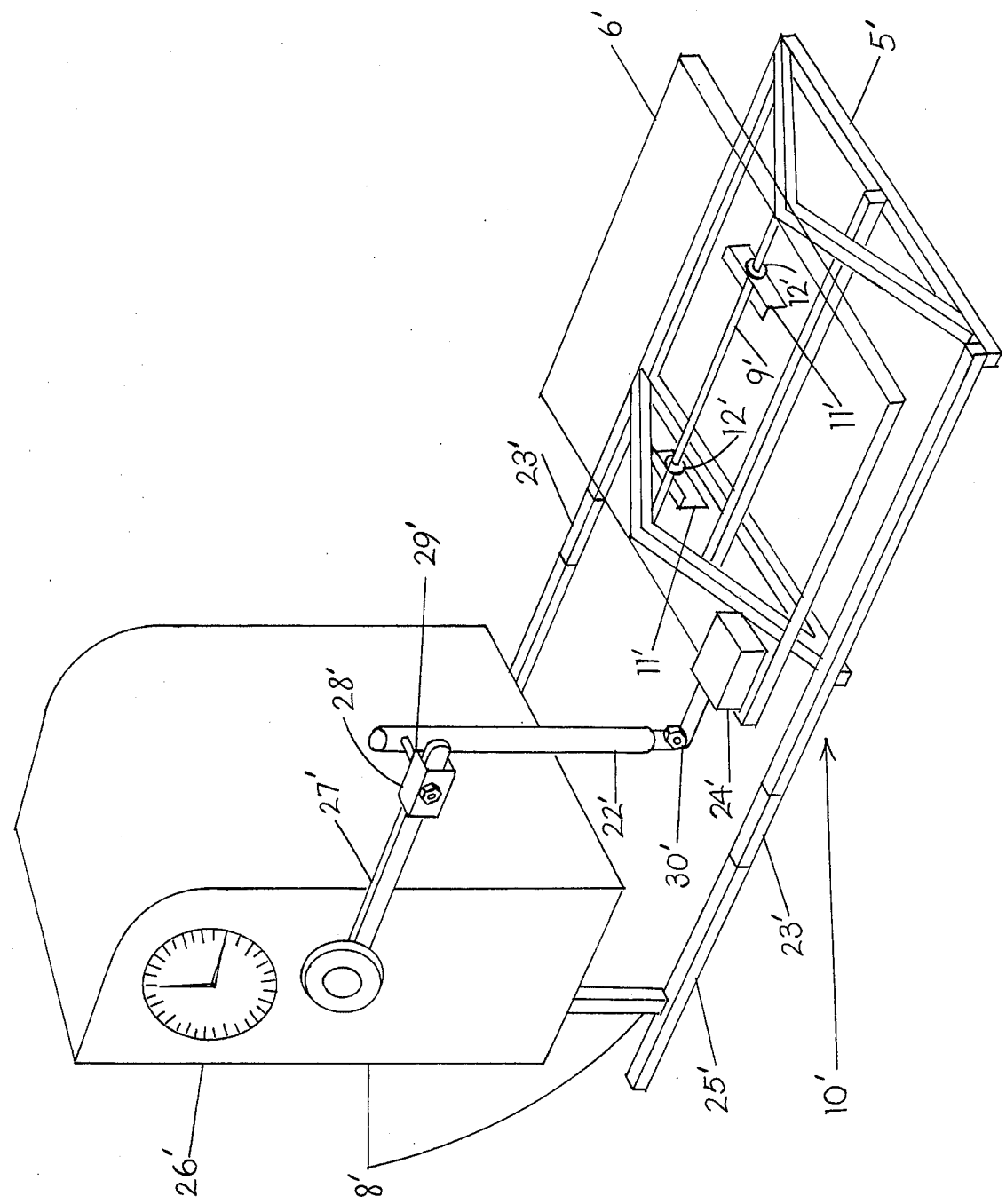

MEASURED VARIABLE RESISTANCE TILTBOARD

FIELD OF THE INVENTION

The present invention relates generally to evaluating and teaching human balance skill, and relates more specifically to a tiltboard having a selectively variable and instantaneously measured resistance to platform movement.

DESCRIPTION OF THE PRIOR ART

Balance boards have traditionally involved a platform upon which a subject stands or sits which will rock or rotate according to movement of the gravity line of the subject. Large gravity line displacements lead to rapid platform movement and relatively smaller gravity line movements result in less rapid or no platform movement.

The "Variable Resistance Tiltboard", U.S. Pat. No. 4,548,289, provides resistance against platform rotation that can be adjusted to be relatively large, thus providing a stable surface, or the resistance can be adjusted to be relatively small so as to provide a less stable surface. Stated in other terms, by selecting the degree of resistance to be applied against platform rotation, the user of this tiltboard determines the platform angular velocity which will accompany a given subject gravity line placement on one side of the platform's pivotal axis.

The changing of the relative stability of the platform of the variable resistance tiltboard allows subjects of differing balance skill to practice maintaining stable posture at their given skill level. A greater degree of resistance to platform movement allows the subject more gravity line movement while remaining stable. The subject is aware of these changes in gravity line movement through sensations of muscle tension, joint motion, and skin pressure detection. The more steady platform allows the subject a greater degree of the above sensations while they are maintaining stable posture. The less stable platform will start to rotate and thereby provide a falling sensation detected with aid from the eyes and inner ears if a subject allows large gravity line movements.

In a variable resistance tiltboard as described in U.S. Pat. No. 4,548,289 the resistance to platform rotation is provided by a resistance element which has no associated means for instantaneously measuring the resistance that is applied against the platform. Therefore, although the user knows the platform angular velocity which will accompany a given subject gravity line placement, the user has no way of directly determining the resistance being applied against platform movement at any given time during the balance task. This resistance must be deduced by placing differential weight in foot pounds on one side of the platform axis of rotation and recording the resulting angular velocity at different resistance settings. These calibrations are compared to recorded platform angular velocities during subject use in order to calculate the differential weight in foot pounds on one side of the platform axis of rotation as the subject's gravity line moves.

The above mentioned variable resistance tiltboard provides useful balance practice. However, the requirement that the resistance applied against platform rotation as the subject shifts their weight be deduced from observed platform angular velocities causes delays and inaccuracies. The angular velocity must be accurately observed and recorded, and then it must be compared to a calibration chart. After completing this conversion process, the tester has obtained only one resistance measurement which applies only to the time period over which the angular velocity was observed. This conversion process presents a barrier to quick, efficient, and accurate measurement of the many changes in resistance as the subject shifts their gravity line during a balance task. Such a conversion process also removes the tester from the immediate and precise data that can be used to give the subject prompt feedback on their performance and can be used to observe subtle changes in performance throughout a balance task. A variable resistance tilt-board is needed which has the ability to instantaneously measure and record resistance being applied against platform movement such that a resistance-over-time graph can be generated to aid in the analysis of balance skill.

SUMMARY OF THE INVENTION

The present invention provides a variable resistance tiltboard that is designed to satisfy the aforementioned need. The invention embodies a tiltboard whose rotation about its axis is opposed by a resistance which is measured instantaneously. The present invention provides a force measurement apparatus that operates in conjunction with the resistance element such that the instantaneous force imparted by the resistance element against platform movement can be determined and recorded.

A preferred embodiment of this device involves using an exercise dynamometer to resist platform rotation. This can be accomplished by clamping the resistance arm of a dynamometer to a rod which is in turn clamped to the platform on one side of the pivot. Adjusting the dynamometer control to provide comparatively large resistance to movement of the dynamometer lever arm provides a relatively stable platform. Likewise, adjusting the dynamometer control to provide a comparatively small resistance against movement of the dynamometer lever arm will result in a relatively unstable platform. In both cases the force of the resistance applied against platform rotation is measured by the dynamometer. A recorder or computer that interfaces with the dynamometer can be used to record the exact resistance throughout the period of the balance task.

Another preferred embodiment that meets the need for instantaneous measurement of the resistance that is applied against platform rotation involves the use of a viscous damping device similar to the resistance element in referenced U.S. Pat. No. 4,548,289. In this embodiment, strain gauges can be attached to a rod which connects the damping device to the platform. This strain gauge placement allows instantaneous measurement of the resistance being provided through the connecting rod. In this case the connecting rod undergoes stress and deformation in proportion with the given level of resistance imparted to it by the damping device. This stress, and the corresponding resistance, can be recorded by a computer associated with the strain gauge circuitry to generate a resistance-over-time graph for the period of a balance test.

Accordingly, it is an object of the present invention to provide an improved variable resistance tiltboard for the objective analysis of human balance reactions.

It is another object of the present invention to provide an improved variable resistance tiltboard which provides instantaneous measurement of the resistance applied against platform rotation.

It is another object of the present invention to provide an improved variable resistance tiltboard which provides ease of recording the resistance applied against platform rotation as that resistance varies during a subject balance task.

BRIEF DESCRIPTION OF THE PREFERRED EMBODIMENT

FIG. 2 is a perspective view of a second preferred embodiment.

DETAILED DESCRIPTION OF THE PREFERRED EMBODIMENT

Figure 1:
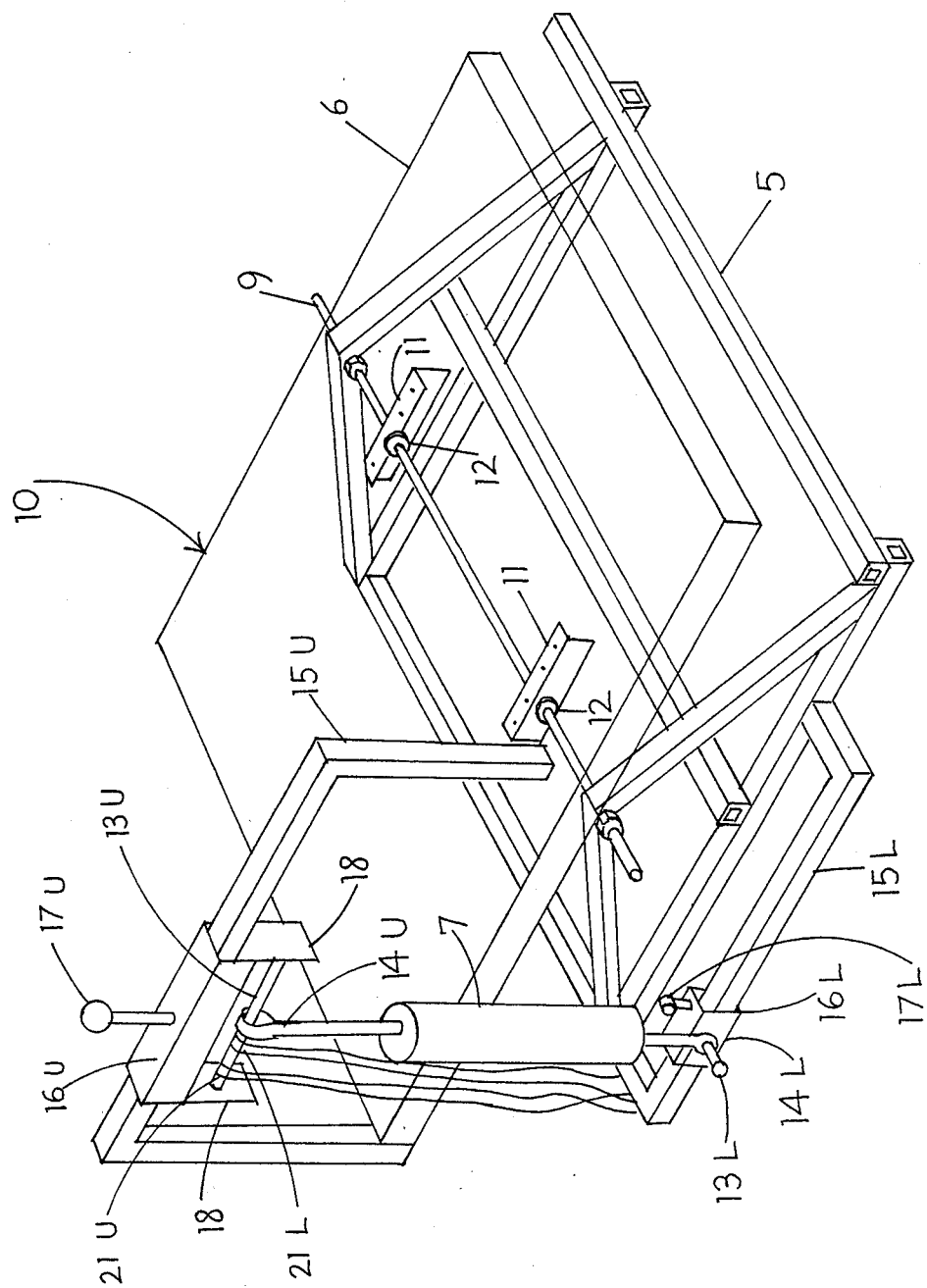
FIG. 1 is a perspective view of a preferred embodiment of the present invention.

Referring now to the drawings in which like numbers indicate like elements in both drawings, FIG. 1 shows a measured variable resistance tiltboard 10 constructed in accordance with the present invention. The measured variable resistance tiltboard 10 includes a platform 6 pivotably supported above a base 5 and a resistive device in the form of a conventional automotive shock absorber 7, which is attached to both support base 5 and platform 6.

The tiltboard 10 further comprises a support rod 9 which is attached to base 5. Brackets 11, which contain bearings 12, are mounted on the bottom of platform 6 such that support rod 9 passes through the bearings 12 and allows rotation of platform 6 relative to base 5 about the axis described by support rod 9.

In FIG. 1 the shock absorber 7 has upper and lower connecting bolts 13U and 13L passing through upper and lower shock absorber eyelets 14U and 14L. Lower connecting bolt 13L is parallel to the support rod 9 and is attached to lower sliding rail 15L. Upper connecting bolt 13U is perpendicular to support rod 9 and is attached to upper sliding collar 16U. Upper and lower sliding collars 16U and 16L can be moved along upper and lower sliding rails 15U and 15L to be positioned differing distances along an axis which is perpendicular to the axis of rotation of platform 6. Upper and lower lock keys 17U and 17L may be tightened at any given distance from support rod 9 to hold upper and lower sliding collars 16U and 16L at the selected distances from the support rod 9.

It will be understood that movement of upper and lower sliding collars 16U and 16L will cause a corresponding movement of shock absorber 7 along the upper and lower sliding rails 15U and 15L and along the axis that is perpendicular to support rod 9. This differential positioning of shock absorber 7 will allow the resistance provided by shock absorber 7 to be expressed through different lever arms and therefore apply more or less resistance against platform 6 movement.

Upper sliding collar 16U has two collar extensions 18 which are in planes parallel to the axis described by support rod 9. Upper connecting bolt 13U is attached to collar extensions 18 at both ends. Upper and lower strain gauges 21U and 21L are affixed to top and bottom of upper connecting bolt 13U with collar extensions 18.

It will be understood that application of resistance against platform 6 by shock absorber 7 will create stress and deformation of upper connecting bolt 13U. Resistance applied by the shock absorber 7 to platform 6 as the shock absorber 7 is shortening will deform upper connecting bolt 13U such that its middle is bent upward. Conversely, resistance applied by the shock absorber 7 to platform 6 as the shock absorber 7 is lengthening will deform upper connecting bolt 13U such that its middle will be bent downward. The upward or downward bending of upper connecting bolt 13U will result in deformation of strain gauges 21U and 21L. Such strain gauge deformation causes instantaneous changes in electrical inputs to strain gauge circuitry which can be used to measure the forces applied against platform 6 by shock absorber 7.

FIG. 2 illustrates a second embodiment 10' employing a platform 6' which is pivotably supported above a base 5'. In this case there is a connecting rod 22' which has platform connecting rod clamps 24' and 28' on both ends. The lower of the connecting rod clamps 24' is tightened around platform 6'. This second embodiment also includes a resistive exercise dynamometer 8' which is comprised of a dynamometer base 25', a dynamometer module 26' which provides resistance and force measurement, and a dynamometer lever arm 27'. The higher of the connecting rod clamps 28' is tightened about dynamometer lever arm 27' thus allowing platform connecting rod 22' to require that platform 6' and dynamometer lever arm 27' move synchronously. Dynamometer 8' is positioned such that the axis of lever arm 27' rotation is perpendicular to the axis of platform 6' rotation.

There are base connecting rods 23' which are attached to the dynamometer base 25' and to the tiltboard base 5' thus allowing no relative movement between dynamometer module 26' and tiltboard base 5'. Base connecting rods 23' between dynamometer base 25' and tiltboard base 5' further ensure that all movement of platform 6' is associated with movement of dynamometer lever arm 27'. Platform connecting rod clamps 24' and 28' are attached to connecting rod 22' with clamp connecting bolts 29' and 30' which are perpendicular to the axis of rotation of platform 6' and which allow for rotation of platform connecting rod 22' about the axis of clamp connecting bolts 29' and 30'.

Resistive exercise dynamometers are designed to allow a subject to push against the lever arm during active exercise while providing a measured resistance against such exercise. It will be understood that in this case rotational forces applied to the surface of the platform 6' will attempt to move platform connecting rod 22' as the platform 6' rotates, and that platform connecting rod 22' movement will attempt to rotate dynamometer lever arm about its axis of rotation. The dynamometer module 26' will provide an instantaneously measured resistance against the above mentioned rotation of platform 6'. The level of resistance applied against a given angular velocity of platform 6' can be altered by adjusting the resistance which dynamometer module 26' provides against the rotation of the dynamometer lever arm 27'.

In both preferred embodiments 10 and 10', differential weight that is placed on one side of the pivotal axis of platform 6 and 6' will apply a rotational force to the platform. This rotational force will be opposed by a resistance which is proportional to and in the opposite direction of the rotational force. In both embodiments the resistance against the rotation of platform 6 and 6' can be adjusted to differing levels. In both embodiments the resistance applied against the rotation of platform 6 and 6' is measured instantaneously and could be recorded as a resistance-over-time graph on associated recorders or computers.

The preferred embodiments of the present invention have been disclosed by way of example and it will be apparent that various changes may be made in the form, construction, and arrangement of parts without departing from the spirit and scope of the appended claims.

I claim:

1. In a variable resistance tiltboard including a platform pivotably supported above a base, and variable resistance means for providing a selectively variable resistance to the movement of said platform relative to said base operatively associated with said platform and said base, the improvement which comprises:

measuring means operatively associated with said platform and said variable resistance means for the instantaneous determination of the force applied by said variable resistance means against movement of said platform.

2. The variable resistance tiltboard as described in claim 1, wherein said measuring means comprises strain gauges attached to a connecting member between said platform and said variable resistance means.

3. In a variable resistance tiltboard including a platform pivotably supported above as a base, and variable resistance means for providing a selectively variable resistance to the movement of said platform relative to said base, the improvement comprises:

said variable resistance means including measuring means for instantaneously determining the force applied by said variable resistance means against movement of said platform.

4. The variable resistance tiltboard as described in claim 3, wherein said variable resistance means comprises:

a resistive exercise dynamometer; and
a member being connected at said platform and at a lever arm of said dynamometer for resisting said platform movement.

5. The variable resistance tiltboard as described in claim 4, further comprising members being connected at said base and at a support base of said dynamometer for preventing movement of said base relative to said dynamometer.

* * * * *